United States Patent [19]

Tavs et al.

[11]  4,183,871

[45]  Jan. 15, 1980

[54] PRODUCTION OF ALDEHYDES AND ALCOHOLS BY THE OXO METHOD

[75] Inventors: Peter Tavs; Wilhelm Kniese, both of Limburgerhof; Hans Nienburg, Ludwigshafen, all of Fed. Rep. of Germany

[73] Assignee: Badische Anilin-& Soda-Fabrik Aktiengesellschaft, Fed. Rep. of Germany

[21] Appl. No.: 568,930

[22] Filed: Apr. 17, 1975

Related U.S. Application Data

[63] Continuation of Ser. No. 262,559, Jun. 14, 1972, abandoned, which is a continuation of Ser. No. 822,311, May 6, 1969, abandoned.

[30] Foreign Application Priority Data

May 9, 1968 [DE]  Fed. Rep. of Germany ....... 1768391

[51] Int. Cl.$^2$ ............................................. C07C 45/02
[52] U.S. Cl. ............................... 260/604 HF; 568/909
[58] Field of Search .................................. 260/604 HF

[56]  References Cited

U.S. PATENT DOCUMENTS

| | | | |
|---|---|---|---|
| 3,239,566 | 3/1966 | Slaugh et al. ................. | 260/604 HF |
| 3,239,569 | 3/1966 | Slaugh et al. ................. | 260/604 HF |
| 3,278,612 | 10/1966 | Greene ........................... | 260/604 HF |
| 3,515,757 | 6/1970 | Sibert ............................ | 260/604 HF |
| 3,527,809 | 9/1970 | Pruett et al. .................. | 260/604 HF |

*Primary Examiner*—James O. Thomas, Jr.
*Assistant Examiner*—G. T. Breitenstein
*Attorney, Agent, or Firm*—Keil & Witherspoon

[57]  ABSTRACT

Production of aldehydes and alcohols by hydroformylation of olefinically unsaturated compounds with carbon monoxide and hydrogen at elevated temperature and superatmospheric pressure in the presence of carbonyl complexes of metals of group 8 of the Periodic System which have been modified with trisubstituted phosphines in which two substituents are lower alkyl radicals and the third substituent is a higher aliphatic radical. Aldehydes and alcohols are known to be solvents; they are used on a large scale for the production of plasticizers for polyvinyl chloride.

9 Claims, No Drawings

PRODUCTION OF ALDEHYDES AND ALCOHOLS BY THE OXO METHOD

This is a continuation of application Ser. No. 262,559 filed June 14, 1972 and now abandoned, which is a continuation of Ser. No. 822,311, filed May 6, 1969, now abandoned.

This invention relates to a process for the production of aldehydes and alcohols by hydroformylation of olefinically unsaturated compounds with carbon monoxide and hydrogen in the presence of carbonyl complexes of metals of group 8 of the Periodic System which have been modified by sutstituted phosphines.

The oxo synthesis in which olefins are reacted with carbon monoxide and hydrogen in the presence of cobalt carbonyl compounds as catalysts is a method for the production of aldehydes and alcohols which has been generally adopted in industry. The process has the disadvantage that some branched aldehydes and alcohols, which are less desirable, are formed. A number of methods are already known in which a high proportion of linear aldehydes and alcohols are obtained. Thus in UK patent Specification No. 903,589 it is stated that a high proportion of linear compounds is obtained when the reaction is carried out at temperatures of from 110° to 130° C. It is a disadvantage, however, that only relatively low conversions are achieved at low temperatures. According to another known method (British Patent Specification No. 1,045,679) a high proportion of linear products is obtained by using high pressures, for example from 500 to 1200 atmospheres. The use of such high pressures is however uneconomical. Moreover, it is known from U.S. Pat. No. 2,694,735 that the hydroformylation of propylene proceeds in favor of the formation of linear products when it is carried out in the presence of ketones. This however necessitates an additional stop for the recovery of the ketones. It is also disclosed in U.S. Pat. Nos. 3,310,576, 3,311,598, 3,239,566, 3,239,569, 3,239,570 and 3,239,571 that when carbonyls of metals of group 8 of the Periodic System which have been modified by phosphines, arsines or stibines are used in the reaction, mainly linear oxygenated compounds are obtained. Finally tertiary phosphines in which the phosphine group is part of a heterocyclic ring are described in British Patent Specification Nos. 1,110,549 and 1,109,787 as modifying agents for hydroformylation catalysts. All conventional phosphine-modified hydroformylation catalysts have the disadvantage however that the reaction takes place in their presence much more slowly than in the conventional reaction in the presence of cobalt carbonyls.

We have now found that aldehydes and alcohols are obtaned more advantageously than hitherto in the oxo synthesis of olefinically unsaturated compounds with carbon monoxide and hydrogen at elevated temperature and superatmospheric pressure in the presence of carbonyl complexes of metals of group 8 of the Periodic System which have been modified with trisubstituted phosphines, by using carbonyl complexes of metals of group 8 of the Periodic System which have been modified with tertiary phosphines in which two of the substituents are lower alkyl radicals and the third substituent is a higher aliphatic radical.

The new process has the advantage that aldehydes and alcohols having linear carbon chains are mainly obtained. Moreover the process has the advantage over those using catalysts modified with tri-n-butyl phosphines that the reaction proceeds more quickly.

It is preferred to use aliphatic, cycloaliphatic or araliphatic olefinically unsaturated compounds having from two to twenty carbon atoms, particularly from two to sixteen carbon atoms. The preferred olefinically unsaturated compounds may have more than one double bond, for example two non-conjugated double bonds or substituents which are inert under the reaction conditions such as alkoxy groups having one to four carbon atoms, carboxyl groups, carbalkoxy groups having from two to nine carbon atoms or nitrile groups. Olefinically unsaturated compounds which have hydrocarbon structure are preferred as starting materials. Olefins having from two to twenty, particularly from two to sixteen, carbon atoms, have achieved particular industrial importance and especially those having a terminal double bond. Examples of suitable olefinically unsaturated compounds are ethylene, propylene, hexene-1, octene-1, decene-1, cyclohexene, styrene, propenylbenzene, allyl alcohol, allyl methyl ether, methyl crotonate, ethyl acrylate, acrylonitrile and olefin mixtures such as occur in the oligomerization of propene and butene, for example the products known as trimeric propylene or codibutylene.

Carbon monoxide and hydrogen are generally used in a ratio by volume of from 1:1 to 1:10, particularly from 1:1 to 1:3.

It is possible to use the olefinically unsaturated compounds and the mixture of carbon monoxide and hydrogen in stoichiometric amounts. It is advantageous however to use the mixture of carbon monoxide and hydrogen in excess, for example up to 500 mole%.

The reaction is carried out with advantage at temperatures of from 140° to 250° C. Particularly good results are obtained by maintaining temperatures of from 170° to 230° C. Good results are obtained when the reaction is carried out at pressures of from 30 to 350 atmospheres. Pressures of from 60 to 300 atmospheres are advantageously used.

It is possible to carry out the reaction without the additional use of solvents. In this case the olefinically unsaturated compounds used serve as solvents. On the other hand it is possible to use solvents which are inert under the reaction conditions, for example cyclohexane or xylene, as solvents. In industry it is advantageous to use the substance obtained as reaction product as the solvent.

The reaction is carried out in the presence of a carbonyl complex of a metal of group 8 of the Periodic System which has been modified by a trisubstituted phosphine in which two of the substituents are lower alkyl radicals and the third substituent is a higher aliphatic radical. Preferred carbonyl complexes of metals of group 8 are those of iron, cobalt, rhodium or palladium. Particularly good results are obtained with cobalt and rhodium carbonyl complexes, expecially cobalt carbonyl complexes. It has proved to be suitable for the atomic ratio of metal to phosphorus in the catalyst to be from 1:1 to 1:6, particularly from 1:1 to 1:3.

Preferred trisubstituted phosphines for use as modifying agents are those in which two substituents are alkyl radicals having one to four carbon atoms, preferably methyl or ethyl radicals and particularly at least one methyl radical, and the third substituent is a higher aliphatic radical having from eight to thirty, particularly from twelve to twenty-four, carbon atoms. The higher aliphatic radical may have substituents which are inert under the reaction conditions such as hydroxyl groups or alkoxy groups having from one to four carbon atoms. Particularly good results are obtained when the third substituent is an alkyl radical having the said number of carbon atoms. The alkyl radical may be linear or branched.

It is preferable to use from 0.1 to 2% by weight of catalyst, calculated as catalyst metal, with reference to the amount of olefin used. Amounts of from 0.2 to 1% by weight have proved to be particularly advantageous. It is possible to prepare the catalysts separately prior to the reactive or to feed the starting materials for the catalyst (such as a fatty acid salt of the metal and one of the said trisubstituted phosphines as a modifying agent) separately to the reaction. The catalyst then forms spontaneously under the reaction conditions.

The process according to this invention may be carried out for example by introducing an olefinically unsaturated compound and a mixture of carbon monoxide and hydrogen, with or without a suitable solvent, into the bottom of a vertical high pressure tube together with the catalyst in the said ratio and carrying out the reaction under the specified conditions of temperature and pressure. The reaction mixture is then released from pressure and separated from the catalyst by distillation. The individual constituents are then isolated from the reaction mixture by a conventional method, for example by distillation. It is possible to return to the reaction unreacted olefin or unused mixture of carbon monoxide and hydrogen.

The aldehydes and alcohols prepared by the process according to the invention are solvents or are suitable for the production of plasticizers for polymers.

The invention is illustrated by the following Examples. The parts specified in the Examples are parts by weight. They bear the same relation to parts by volume as the kilogram to the liter.

EXAMPLE 1

58 parts per hour of octene (containing, per kilogram of octene, 20 g of cobalt ethylhexanoate (85% by weight strength) and 23 g of dimethyldodecyl phosphine) is pumped upward into a high pressure vessel having a capacity of 500 parts by volume. At the same time a gas mixture consisting of carbon monoxide and hydrogen in a volumetric ratio of 1:2 is pumped in at such a rate that a pressure of 80 atmospheres is maintained. Moreover a temperature of 190° C. is maintained. 70.5 parts per hour of a discharge having a refractive index of $n_D^{20}=1.4281$ is obtained. A sample of the discharge exhibits a strong band at 1950 cm$^{-1}$ in the infrared spectroscope. It is the complex of cobalt, carbon monoxide and dimethyldodecyl phosphine. According to gas chromatographic analysis, the discharge contains 16% by weight of unreacted octene, 7.5% by weight of octane, 3% by weight of $C_9$ aldehydes and 69.5% by weight of $C_9$ alcohols. The fraction of nonanol-(1) in the $C_9$ alcohols is 87%.

COMPARATIVE EXAMPLE

The procedure of Example 1 is adopted but octene-(1) containing per kilogram 20 g of cobalt ethylhexanoate (85% by weight strength) and 20 g of tri-n-butyl phosphine is used as the starting material. 67 parts per hour of a mixture which according to the gas chromatographic analysis contains 22.5% by weight of unreacted ocetene-(1), 10% by weight of octane, 2.5% by weight of nonanals and 56% by weight of nonanols, is obtained. The conversion of octene-(1) and the yield of nonanals per unit of time is therefore much less than in Example 1.

We claim:

1. In a process for the production of aldehydes and alchols by the hydroformylation of aliphatic, cycloaliphatic or araliphatic olefinically unsaturated compounds having up to twenty carbon atoms with carbon monoxide and hydrogen in a ratio by volume of carbon monoxide to hydrogen of from about 1:1 to 1:10 and a mole ratio of the $CO/H_2$ mixture to the olefinic unsaturated compound of from about 1:1 to 1:5 at a temperature of from 140° to 250° C. and at a pressure of from 30 to 350 atmospheres in the presence of a carbonyl complex of cobalt which has been modified by a trisubstituted phosphine, the improvement which comprises: using a carbonyl complex of cobalt which has been modified with a trisubstituted phosphine in which two substituents are methyl or ethyl, at least one of which is methyl, and the third substituent is an unsubstituted alkyl radical having from eight to thirty carbon atoms or an alkyl radical of eight to thirty carbon atoms substituted by hydroxyl groups or alkoxy groups of one to four carbon atoms, said substituent groups being inert under the reaction conditions the atomic ratio of cobalt to phosphorous in the catalyst being from about 1:1 to 1:6 and the weight ratio of cobalt to olefin being from 0.1 to 2.0:100.

2. A process as claimed in claim 1 wherein an olefin having from two to twenty carbon atoms is used as the starting material.

3. A process as claimed in claim 1 wherein an olefin having from two to twenty carbon atoms and a terminal double bond is used as the starting material.

4. A process as in claim 1 carried out at a temperature of from 170° to 230° C.

5. A process as in claim 1 carried out at a pressure of from 60 to 300 atmospheres.

6. A process as in claim 1 wherein a trisubstituted phosphine is used as modifying agent in which one of the substituents is an alkyl radical having from twelve to twenty-four carbon atoms.

7. A process in claim 1 wherein an trisubstituted phosphine is used as modifying agent in which one of the substituents is an alkyl radical having from twelve to twenty-four carbon atoms, another substituent is a methyl radical and the third substituent is an ethyl radical.

8. A process as in claim 1 wherein a trisubstituted phosphine in which one of the substituents is an alkyl radical having from eight to thirty carbon atoms, a second substituent is a methyl radical and the third substituent is an ethyl radical is used as the modifying agent.

9. A process as in claim 1 wherein said two substituents are methyl.

* * * * *